United States Patent [19]
Durzan et al.

[11] Patent Number: 5,981,777
[45] Date of Patent: *Nov. 9, 1999

[54] RECOVERY OF TAXANES FROM PLANT MATERIAL

[75] Inventors: Don J. Durzan; Frank F. Ventimiglia, both of Davis, Calif.

[73] Assignee: The Regents of the University of California, Oakland, Calif.

[ * ] Notice: This patent is subject to a terminal disclaimer.

[21] Appl. No.: 08/972,844

[22] Filed: Nov. 18, 1997

[51] Int. Cl.⁶ .................................................. C07D 305/14
[52] U.S. Cl. ........................................... 549/510; 549/511
[58] Field of Search ..................... 549/510, 511

[56] References Cited

U.S. PATENT DOCUMENTS

| | | | |
|---|---|---|---|
| 5,547,866 | 8/1996 | Durzan et al. | 435/123 |
| 5,670,663 | 9/1997 | Durzan et al. | 549/332 |

OTHER PUBLICATIONS

Sinha et al. (1994) *Prog. Drug Res.* 42: 53–132.
Guo et al. (1994) *Biol. Chem. Hoppe. Seyler*, 374(4): 281–7.
Zenkteler, M., et al. "Cytological studies n the regenerating mature female gametophyte of *Taxus baccata L.* and mature endosperm of *Tilia platyphyllos* Scop. in vitro culture," *Acta Sacietatis Botanicorum Poloniae*, 1:161–173 (1970).
Gibson, D. et al. "Initiation and growth of cell lines of *Taxus brevifolia* (Pacific yew)," *Plant Cell Reports*, 12:479–482, 1993.
Fett–Neto, A. et al., "Improved Growth and Taxol Yield in Developing Calli of *Taxus cuspidata* by Medium Composition Modification," *Bio/Technology*, 11:731–734, 1993.
Fett–Neto, A., "Cell Culture of Taxus as a Source of the Antineoplastic Drug Taxol and Related Taxanes," *Biotechnology*, 10:1572–1575, 1992.
Byrde, R., (1979) "Role of Polysaccharide–Degrading Enzymes in Microbial Pathogenicity," Microbial Polysaccharides and Polysaccharases (Chapter 18):422–424 (1991–92) "Technical Information," *Sigma Plant Cell Culture* 49–59.
Rohr, R., "Activation et proliferation des cellules du megagametophyte de Taxus cultive in vitro," *Can. J. Bot.*, 60:1583–1589, 1982.
Durzan and Ventimiglia, In Vitro Cell Dev. Biol. 30:219–227 (1994).

*Primary Examiner*—Ba K. Trinh
*Attorney, Agent, or Firm*—Townsend and Townsend and Crew

[57] ABSTRACT

The present invention provides new methods isolating taxanes and other metabolites from taxane-producing plant materials.

19 Claims, No Drawings

RECOVERY OF TAXANES FROM PLANT MATERIAL

CROSS-REFERENCE TO RELATED APPLICATIONS

This application is related to U.S. Ser. No. 08/277,463, now U.S. Pat. No. 5,547,866 and U.S. Ser. No. 08/601,367, now U.S. Pat. No. 5,670,663, both of which are incorporated herein by reference.

BACKGROUND OF THE INVENTION

The present invention relates to the production and recovery of taxane compounds. In particular, it relates to methods of identification and isolation of taxane-producing plant material.

Taxane compounds, in particular paclitaxel (Taxol™), have significant antitumor activity and have been the focus of investigations to develop these compounds as drugs for the treatment of cancer. These compounds have also been shown to inhibit congenital polycystic kidney disease (Woo et al. *Nature* 368 759 (1994)). Paclitaxel, originally isolated from the bark of the Pacific yew, *Taxus brevifolia*, was recently approved by the Food and Drug Administration for use against ovarian cancer and has also shown activity against breast, lung and other cancers.

Continued testing of paclitaxel and other taxanes require quantities which cannot be obtained from the scarce natural source. *T. brevifolia* is a rare tree, grows slowly, and is not cultivated. In addition, thousands of pounds of bark are required to produce one pound of paclitaxel. Moreover, extraction of the bark is complicated, and product variability occurs.

Because of the scarcity of naturally occurring paclitaxel, numerous investigators have attempted to increase the supply of paclitaxel and other taxanes. For instance, cell suspension cultures of sporophytic tissues have been shown to produce paclitaxel (U.S. Pat. No. 5,019,504). In addition, recent reports describe the total synthesis of paclitaxel (see, Holton et al. *JACS* 116:1597 (1994) and Nicolaou et al. *Nature* 367:630 (1994). These syntheses, however, involve too many steps to be commercially feasible (Flann, *Science* 263:911 (1994)).

Increased availability of taxanes will facilitate investigations to synthesize analogs of paclitaxel or identify other taxanes with similar anti-tumor activity but having improved properties. For instance, paclitaxel is relatively insoluble in aqueous solutions. As a result, paclitaxel is usually dissolved in an oily base of castor oil and alcohol and administered in this form. The identification of related compounds with increased aqueous solubility could provide compounds with better cellular penetration and efficacy than is found with paclitaxel.

Despite advances in the art, availability of paclitaxel and other taxane compounds remains a critical limitation in further investigation and therapeutic use of these compounds. The present invention addresses these and other needs.

SUMMARY OF THE INVENTION

The present invention provides methods of identifying taxane-producing plant material in a sample. The methods comprise contacting the plant material with an antibody which specifically binds taxanes present on or in plant cell walls. Preferred antibodies include TA12, TA13, and TA14, which are commercially available. Typically, the methods further comprise the step of isolating the taxane-producing plant material from other material in the sample. A preferred method for isolating the desired material is with the use of a paramagnetic bead to which a secondary antibody (which recognizes the first antibody) is bound.

In some embodiments, the plant material comprises plant cells, for instance, in vitro tissue culture cells. Any plant known to produce taxanes can be used. Taxus cells are generally preferred. The methods may further comprise isolating high taxane-producing cells from low taxane-producing cells. Thus, cultures comprising substantially only taxane producing cells can be produced.

The invention further provides methods of increasing taxane production in plant cell cultures. The methods comprise growing the plant cell culture in a complete plant growth medium comprising an inhibitory compound, that inhibits cell division and/or stresses the cells by inhibiting cellular metabolism. Exemplary inhibitory compounds include herbicide, such as chlorsulfuron. A preferred concentration for these compounds is generally between about $10^{-12}$M and about $10^{-6}$M. In some embodiments, the action of the inhibitory compound can be counteracted by cell stress reductant that maintains osmotic pressure in the cells, prevents oxidation, inhibits apoptosis, and the like.

Definitions

The term "taxanes" refers to compounds comprising the tricyclic ring nucleus shown by

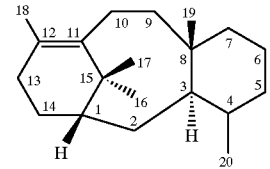

The chemical structure of taxanes and related compounds (e.g., Taxine A) is described in Gueritte-Voegelin *J. Nat. Prod.* 50:9–18 (1987).

Taxanes of the invention can also be identified through the use of antibodies raised against paclitaxel and related compounds. A number of such antibodies are known and are commercially available. Suitable antibodies include TA12, which is specifically reactive with paclitaxel and its C-7 derivatives, and TA14 which cross reacts with paclitaxel, cephalomannine, baccatin III, and 10-deacetylbaccatin III (Kingston et al*J. Nat. Prod.* 53:1–12 (1990)) and TA13 which binds with equal affinity to baccatin III and its 7-epi isomer baccatin V. These antibodies are all commercially available from the Hawaii Biotechnology Group Inc., Aiea, Hi. Taxanes can be further identified by their chromatographic behavior in a "taxane" column and their characteristic UV spectra in the 190 to 600 nm range. Taxane-like activity can be assayed using an in vitro microtubule polymerization assay as described in U.S. Pat. No. 5,019,504.

The term "bound taxanes" refers to taxane compounds produced by a plant cell and that are not significantly extracted by standard solvent extraction methods, but are recovered after hydrolysis of plant materials. Without wishing to be bound by any particular theory, such taxanes are thought to be covalently bound to cell wall and other components and released by, for instance, hydrolysis of the cell wall components. Hydrolysis is typically carried out by enzymatic cleavage. Other methods of releasing bound cell wall components can also be used.

As used herein "taxane-producing plant material" includes any plant material from which taxanes may be isolated. Such material includes, but is not limited to, in vitro cell cultures, plant tissues, whole plants, and cellular debris (e.g., cell walls, wood pulp, waste products in paper manufacturing and the like).

As used herein a cell culture comprising "substantially only taxane-producing cells" is a culture in which at least about 30%, more typically at least about 60%, usually at least about 75%, and preferably at least about 90% of the living cells in the culture produce taxanes, as determined by their ability to specifically react with anti-taxane antibodies.

As used herein an "inhibitory compound" is a compound that inhibits cell cycling in plant cells and thus maintains the cells in interphase. As a result of decreased cell division, more cellular energy is available for production of taxanes. Typically, inhibitory compounds of the invention are herbicides that inhibit cellular metabolism thus inhibiting production of metabolites necessary for vigorous cell growth. The increased stress on the plant cells caused by these compounds leads to increased taxane production. Any of a number of herbicides or other inhibitory compounds can be used. Examples of herbicides include chlorsulfuron and thiadiazuron. Examples of compounds that inhibit protein synthesis include cyclohexamide and homoharringtonine, and the like.

A "composition capable of extracting taxanes" is any composition, typically an organic solvent such as methanol, which can be used to extract taxanes and related compounds from plant tissues containing such compounds. A number of suitable compositions are known in the art. For instance, U.S. Pat. No. 5,445,809 describes the isolation of taxanes using a "reactor compound" containing paclitaxel precursors. U.S. Pat. No. 5,440,055 describes the use of "CoNC fluids" as solvents. As defined in that patent CoNC fluids are comprised of materials which exist as gases at ambient conditions, such as the gases carbon dioxide and nitrous oxide. When such gases are compressed and brought to conditions near or above their critical pressures and temperatures, such gases exhibit enhanced solvating power.

The phrase "specifically reactive with", when referring to the interaction between an antibody and an antigen, such as a taxane ring, refers to a binding reaction between the antigen and the antibody which is determinative of the presence of the antigen in the presence of a heterogeneous population of other compounds. Thus, under designated immunoassay conditions, the specified antibodies bind to a particular antigen against which they were developed and do not bind in a significant amount to other compounds present in the sample.

DESCRIPTION OF THE PREFERRED EMBODIMENT

The present invention provides new methods of identifying and isolating sources of taxanes from plant materials. The method also provides improved cell culture media and methods that provide increased taxane production. Plant material used in the methods of the invention is typically derived from members of the genus Taxus. It has been found that a number of genera in the order Coniferales produce significant amounts of taxanes and are therefore good sources of taxanes (see, e.g., U.S. Pat. No. 5,670,663). Thus, one of skill will recognize that the methods can be used with any plant material known to produce (or suspected of producing) taxanes.

Identification of Taxane Producing Cells

According to one aspect of the invention, antibodies specifically reactive with taxanes are contacted with the appropriate plant material. Any plant material suspected of containing taxanes can be used. For instance, cell cultures, macerated plant tissue, cell debris from tissue cultures, wood pulp, and waste products in paper manufacturing can be used.

Any of a number of antibodies which are specifically reactive with taxanes can be used in the methods of the invention. A preferred antibody is TA14 available from Hawaii Biotechnology Group is particularly useful for this purpose. The cross-reactivity of polyclonal anti-taxane (TA11) and taxol- (TA12), baccatin III- (TA13), or "generic taxane"-specific (TA14) monoclonal antibodies as determined by indirect competitive immunoassays is set forth in Table 1. All of these antibodies are available from Hawaii Biotechnology group.

TABLE 1

| Taxane | $IC_{50}{}^a$ (nM) | | | |
|---|---|---|---|---|
|  | TA11 | TA12 | TA13 | TA14 |
| Taxol ® (paclitaxel) | 0.5 | 10 | >316 | 7 |
| 10-deacetyltaxol | 0.7 | 15 | >333 | 10 |
| 7-epi-10-deacetyltaxol | 1.2 | 25 | >333 | 15 |
| 7-xylosyl-10-deacetyltaxol | 1.8 | 30 | >286 | 17 |
| 7-epi-taxol | 8.0 | 80 | >316 | 50 |
| cephalomannine | 1.0 | 220 | >325 | 8 |
| baccatin III | >511 | >511 | 10 | 12 |
| baccatin V | >460 | >460 | 10 | 10 |
| 10-deacetylbaccatin III | >551 | >551 | 230 | 21 |
| 7-epi-10-deacetylbaccatin III | 34 | >496 | 150 | 27 |
| Taxotere ® (docetaxel) | NT | >318 | >318 | 10 |
| 2-debenzoyl-2-(p-trifluoromethylbenzoyl) taxol | NT | >293 | >293 | >293 |
| 20-acetoxy-4-deacetyl-5-epi-20, O-secotaxol (Meerwein product) | NT | >310 | >310 | >293 |

$^a$Cross-reactivity is expressed as the concentration of analyte required to inhibit antibody binding to solid phase antigen by 50% ($IC_{50}$) in the indicated competitive immunoassay. Values expressed as > x represent the highest concentration tested (either 270 or 300 ng/ml).

In preferred embodiments, cell suspension cultures are used. The methods of the invention are particularly useful in isolating cells which produce taxanes, thereby producing cultures comprising substantially only taxane-producing cells. The antibodies bind to taxanes bound to the cell wall of target cells and are thus useful in identifying the taxane-producing cells. The cells bound by the antibodies can then be isolated from non-specifically reactive cells by any of a number of standard techniques. For instance, the antibody can be labeled to facilitate identification and subsequent isolation of the cells. Any of a number of methods useful in identifying antibody-bound cells can be used. The antibodies can be used, for instance, in competitive inhibition enzyme immunoassays (CIEIA). Methods of isolating the desired cells include, use of paramagnetic beads, immunoaffinity columns, fluorescence activated cell sorting, density gradient centrifugation and the like.

Preferred methods involve the use of paramagnetic beads to separate cell suspensions. Typically, beads coated with a secondary antibody (e.g., coated with anti-mouse, anti-rat or anti-rabbit antibodies) are used to identify cells bound by anti-taxane antibodies. Such beads are available, for instance, from Dynal, Inc. Lake Success, N.Y. Brun et al. Blood 1990;76(11):2397–2403. Such methods are described, for instance, in U.S. Pat. No. 4,910,148, Metzger et al. Ann.N.Y.Acad.Sci 651:75–77 (1992), Rasmussen et al. Journal of Immunological Methods 146:195–202 (1992), and Funderud et al. European Journal of Immunology 20:201–206 (1990).

The cells identified and isolated using the methods described above can be further separated into relatively high producing cells and relatively low producing cells. The relatively high producing cells can be identified by the amount of binding of anti-taxane antibodies. In those embodiments in which paramagnetic beads are used, the cells with the highest concentration of beads bound to them can be separated from those with lower concentrations using a number of standard techniques. For instance, density gradients in low speed centrifugation or varying magnetic fields can be used to isolate relatively high producing cells.

Cell Cultures of the Invention

In some embodiments, tissue cultures derived from the plant tissue of interest are established. Methods for establishing and maintaining plant tissue cultures are well known in the art (see, e.g., P. R. White, 1954, *Cultivation of Animal and Plant Cells* Ronald Press, New York). Typically, the plant material is surface-sterilized prior to introducing it to the culture medium. Any conventional sterilization technique, such as chlorinated bleach treatment can be used. In addition, antimicrobial agents may be included in the growth medium. Under appropriate conditions plant tissue cells form callus tissue, which may be grown either as solid tissue on solidified medium or as a cell suspension in a liquid medium. Metabolic products of the callus, such as taxol or other alkaloids, may be isolated from the callus cells or from the culture medium using known techniques (see, e.g., U.S. Pat. No. 5,019,504).

A number of suitable culture media for callus induction and subsequent growth on aqueous or solidified media are known. Exemplary media include standard growth media, many of which are commercially available (e.g., Sigma Chemical Co., St. Louis, Mo.). Examples include Schenk-Hildebrandt (SH) medium, Linsmaier-Skoog (LS) medium, Murashige and Skoog (MS) medium, Gamborg's B5 medium, Nitsch & Nitsch medium, White's medium, and other variations and supplements well known to those of skill in the art (see, e.g., *Plant Cell Culture*, Dixon, ed. IRL Press, Ltd. Oxford (1985) and George et al., *Plant Culture Media*, Vol 1, Formulations and Uses Exegetics Ltd. Wilts, UK, (1987)). For the growth of conifer cells, particularly suitable media include 1/2 MS, 1/2 L.P., DCR, Woody Plant Medium (WPM), Gamborg's B5 and its modifications, DV (Durzan and Ventimiglia, In Vitro *Cell Dev. Biol.* 30:219–227 (1994)), SH, and White's medium.

As noted above, the plant cells used in the present invention can be any member of the order Coniferales. Members of the genus Taocus are preferred. As explained in U.S. Pat. No. 5,547,866, a preferred source of taxane producing cells are "haploid-derived" cells, that is, cells that are homozygous diploid or polyploid cells which arise from haploid cells either spontaneously or by manipulation of the cultures. The haploid tissues are usually female gametophytic tissue from immature seeds (e.g., archegonial initials, oocytes or a combination thereof). The tissue is grown in nutrient media for selection of haploid cells and their derivatives, as distinct from cells of the diploid sporophyte (e.g., embryo, cambium, needles, bark, roots).

For the recovery and scale-up of haploid-derived cells, a medium which substantially lacks nitrates is preferably used. It is understood that modifications can be made in these media, such as substitutions of salts, e.g., addition or deletion of various components or alteration of proportions. Suitable media, such as TMH and DV media, are described in detail in U.S. Pat. No. 5,547,866.

The culture media used in the methods of the invention may be solid, semi-solid or liquid. Any gelling agent (e.g., agar, Gelrite and the like) commonly used to solidify media can be used. For establishment of cell suspension cultures, an inoculation density of about 1 gm per 100 ml medium is preferably used. Cells are subcultured every 10 to 14 days or sooner to scale-up for cell mass.

Once a desired cell culture is established it can be easily scaled-up for growth in bioreactors and production of taxanes on a production scale. For instance, radial flow cultures can be used. Process controls in such bioreactors enable environmental, physiological and physical parameters of the culture system to be mechanized and optimized for maximum output of the desired products. For a general discussion of bioreactors and methods useful for the present invention see Shuler and Karg *Bioprocess Engineering—Basic Concepts* (Prentice-Hall, Englewood Cliffs, N.J. 1992).

Increasing Taxane Production

Increased taxane production can be achieved in a number of ways. In some embodiments, this is achieved by simply withholding nutrients and subculture routines. Withholding of subculture leads to a slow browning of cells and to the leakage of metabolites into the culture medium.

In certain embodiments of the invention, plant cell cultures are treated with inhibitory compounds that maintain the cells in interphase and thus prevent the cells from diverting resources to cell division. In addition, the inhibitory compounds stress the plant cells by inhibiting metabolism, thus leading to increased taxane production. Typically, inhibitory compounds include herbicides such as chlorsulfuron and thiadiazuron. Protein synthesis inhibitors such as cyclohexamide and homoharringtonine are also conveniently used. In addition, antibiotics such as kanamycin, actinomycin, and the like can be used. The concentration of the compound used is ideally high enough to stress the cells and/or prevent cell division, but not high enough to be lethal to the majority of the cells in the culture. Generally, the concentration of the compound used to maintain the cells in interphase will be present in the plant growth medium at a concentration between about $10^{-12}$ M and about $10^{-2}$ M, usually between about $10^{-12}$M and about $10^{-4}$ M. In the case of chlorsulfuron, the concentration used is typically between about $10^{-12}$ M to about $10^{-6}$ M, usually between about $10^{-12}$ M to about $10^{-7}$ M.

When the inhibitory compounds are included in plant growth media of the invention, it is sometimes desirable to include compounds cell stress reductants. These compounds may act by protecting osmotic balance in the cell, by preventing oxidation of taxanes, or by inhibiting apoptosis. Examples of compounds useful for this purpose include zinc, betaine, polyamines, colchicine, cyclodextrins, and the like. Agents which can be used as osmotic pressure protectants are known in the art and include amino acids, such as proline, and sugars, such as trehalose, inositol, or mannitol. Examples of compounds known to inhibit apoptosis include superoxide dismutase, thioredoxin, $n^{\alpha}$-tosyi-lys ciforomethyl ketone, n-acetyl-1-cysteine, aphidicolin, aurin tricarboxylic acid, bapta/am, caffeine, calpain inhibitor I, calpain inhibitor II, calyculin a, Catalase, cyclosporin a, 3,4-dichloroisocoumarin, diisopropylfluorophosphate, N-ethylmaleimide, flunarizine, forskolin, genistein, guanosine 3',5'-cyclic monophosphate, herbimycin a, insulin-like growth factor-I, interleukin-1β, interleukin-6, leupeptin, phenylmethylsulfonyl fluoride phorbol-12-myristate-13-acetate 1-pyrrolidinecarbodithioic acid, and spermine. Typically, these compounds will be present in the medium at a concentration of between about $10^{-7}$ M and about $10^{-2}$ M, usually between about $10^{-5}$ M and about $10^{-4}$ M.

Isolation of Taxanes

Once the cell cultures of the invention are established, standard methods for the isolation of taxanes and related compounds from plant tissues can be used. The particular method used to extract taxanes and related compounds is not critical to the invention. Typically, taxanes are extracted with organic solvents from the particular plant tissue and chromatographically purified. Adsorbent beads may be used to remove the taxanes produced. In addition, particulate matter released by the cells may be used to adsorb the taxanes. The particular adsorbent material is not a critical aspect of the invention, so long as the material provides a sink for removing the end-product from the reaction sequence.

The extraction process typically begins by contacting the tissue to be extracted with an alcohol (e.g., methanol) at elevated temperature, 50° to 55° C. The extract is then concentrated in methanol. Next, the concentrated methanol extract is partitioned between methylene chloride and water. The methylene chloride fraction, containing paclitaxel, is concentrated. The methylene chloride concentrate is dissolved in 50/50 acetone:hexane, and the mixture is filtered to remove insolubles.

The taxanes are then purified from the acetone:hexane mixture using a variety of chromatographic methods. For instance, the purification of paclitaxel is typically carried out using chromatography on Florisil columns in a 70/30 hexane:acetone mixture to separate the paclitaxel containing fractions. The paclitaxel fractions are then concentrated to dryness. Paclitaxel concentrates are crystallized from a methanol:water mixture and then recrystallized from an acetone:hexane mixture yielding 85 to 95% pure paclitaxel. The paclitaxel is then chromatographed on silica gel with either 2.5% isopropanol or 2.5% n-butanol in methylene chloride to yield approximately 98% pure paclitaxel.

Taxanes, referred to here as "bound taxanes" can also be located on the surfaces of various plant cells and tissues. Enzyme treatment of exhaustively extracted tissues yields taxanes that are detectable by HPLC. By contrast, the nonenzymatically treated controls do not yield detectable taxanes. The present invention also provides extraction methods for the recovery of these bound materials. For a description of methods suitable for this purpose see, Durzan and Ventimiglia, In Vitro *Cell Dev. Biol.* 30:219–227 (1994).

The bound compounds left behind by standard extraction methods provide an extended pool that increases the diversity of known taxanes and their precursors. This diversity is a source for potentially new and novel antitumor compounds and/or their synthons. The enzymatically released compounds show an enhanced solubility in polar solvents. Enhanced solubility in polar solvents, in particular aqueous solutions, provides better cellular penetration and pharmaceutical efficacy than is found in the relatively insoluble paclitaxel.

Additionally, enzymatic treatment of taxane productive sources provides digestion products that are useful as catalytic surfaces and elicitors of further taxane production. Protoplasts derived from cells and tissues with digested cell walls are a source of genetically alterable cells that enable the design of genetically superior lines and potentially taxane productive plant products.

The recovery methods of the invention typically use enzymatic cleavage to release bound taxanes. Exemplary enzymes for this use include glycosidases such as pectinase, xylanase, cellulase and the like. Such enzymes are commonly used to digest cell wall components for the production of protoplasts. Other degradative enzymes known to those of skill in the art, such as ligninases, chitinases and the like, can also be used. Other compounds or conditions suitable for the cleavage of chemical bonds in the cell wall or other components of the cell can also be used for this purpose. Suitable methods include the use of strongly oxidizing conditions, acid or alkaline hydrolysis (using either mild or harsh conditions) and the like. Alternatively, irradiation or heat can be used to release the compounds.

The methods used to release bound taxanes may in some cases result in artifactual alteration of the chemical structure of the purified taxanes (see, e.g., Miller *J. Nat. Prod.* 43:425 (1980)). Such alterations can be useful as a source for taxanes with improved chemical and pharmaceutical properties, such as solubility, activity, metabolic half-life and the like. These compounds can also be used as synthons for the synthesis of new taxanes.

Enzymes (e.g. cellulase, pectinase and xylanase) as reagents in "live" cultural conditions, whether continuous or batch, can be used to remove bound taxanes and related alkaloids. The released taxanes can then be isolated by extraction. The enzymatic release of other potential substrates into the culture medium would affect synthesis with a positive or negative effect on total yield. Hence, enzymes can be used for process control (feedforward or feedback) of taxane and related alkaloid production. This can be used to manipulate the culture environment to optimize for rapid growth or maximum yield of desired compounds.

The following examples are intended only to further illustrate the invention and not intended to limit the scope of the invention, which is defined in the attached claims.

EXAMPLE 1

This example demonstrates the separation of *Taxus cuspidata* cells by labeling with Dynal bead labeled anti-taxane antibodies.

A. Materials:

Cells:

About 4 cc of *Taxus cuspidata* callus was grown on Modified B5 medium with kinetin and 2,4D.

Mixed qualities of tissue, off white to moderately brown calli, were used.

Reagent Volumes:

Phosphate buffered saline (PBS) rinses, pH 7.0: 10–12 ml

Antibody reagents: 5 ml PBS:

50 mM Sodium Phosphate Monobasic—Monohydrate FW: 138.00

150 mM Sodium Chloride FW: 58.4

Sodium Phosphate Monobasic—Monohydrate
0.050 moles/liter×138.0 g/mole=6.9 g/liter Sodium Chloride
0.15 moles/liter×58.4 g/mole=8.76 g/liter To obtain two liters, 13.8 g of sodium phosphate monobasic—monohydrate and 17.52 g of sodium chloride were used. The pH was adjusted to 7.0 with NaOH Blocking Buffer:

1% BSA (w/v) (Sigma A-9647)

10% (v/v) Sheep serum (Sigma S-3772) in PBS pH 7.0

Preferably, the blocking buffer is made fresh each time.

Preferably, the serum type of the animal of origin should match the secondary antibody animal of origin. For example, if the secondary antibody used in this protocol were from a rabbit, then the blocking buffer should include serum from a rabbit. The serum helps to block any nonspecific binding of the secondary antibody. Never include any serum that matches the primary antibody type.

Dynal Beads:

Dynabeads M-450, 4.5 micron diameter

Sheep anti-Mouse IgG 4.0×10⁸ beads/ml (approximately)

Dynal, Product #110.01

Dynabeads are superparamagnetic, monodispersed, polymer beads with a hydrophobic surface. The M-450 beads contain about 20% iron. The surface of the beads are coated with a thin polymer shell which encases the magnetic material and provides a defined surface for the adsorption or coupling of various molecules. The beads used in this protocol were coated with sheep anti-mouse IgG molecules.

Washed Dynal Beads:

Before use, the aliquot of beads for this protocol were washed in blocking buffer once. Two hundred and fifty (250) ul of Dynal beads (approximately 1×10⁸ beads) were suspended in 5 ml of blocking buffer and agitated for about 30 seconds. The magnet was used to pull the beads to one side of the tube and the blocking buffer was removed with a pipet.

The "clean" beads were resuspended in 2.5 ml of blocking buffer

Magnet:

Rare Earth Cobalt Magnet

Disc: 1" diameter, 0.375" thickness

Edmund Scientific, stock # P30,963

Polylysine Coated Thermanox Coverslips:

Thirteen (13) mm thermanox coverslips were used and dipped in 1% polylysine (Sigma Chemical Co., Cat. No. P1274), molecular weight range 70,000–150,000, dissolved in reagent grade water (the molecular weight (MW) range is important. Cells adhere to the coverslip with the 70,000–150,000 or 150,000–300,000 MW range. At greater than 300,000 MW, the solution is too viscous to form a good coating. Much smaller MW forms do not attach cells as well). The coverslip was allowed to dry completely at room temperature while on edge. A piece of wood with thin slots worked well as a stand.

The coverslips used were Thermanox coverslips (NUNC, Inc., Naperville, Ill.) available from VWR Scientific, as cat. #: 62407–067.

Primary Control Antibody:

Mouse IgG2a kappa, 1 mg/ml, purified myeloma immunoglobulins (Sigma, Item M-9144) was used. The primary control antibody is used to detect any primary antibody binding that may occur as a result of nonspecific interactions between the antigen directed primary antibody and the cells. For this protocol, Hawaii Biotechnology monoclonal antibodies directed at taxol, baccatin and taxanes were used. These consist primarily (about 95%) of the IgG2a kappa subclass. Therefore, mouse IgG2a kappa, purified myeloma immunoglobulins were used as a control. Theoretically, the selected control antibody should have no affinity for the antigenic targets (taxol, baccatin and taxanes) and preferably have no affinity for any other specific loci on, or in, the cells being tested (for example, in the form of unintended antigen-directed specificity such as would happen if the host animal of the control primary antibodies was exposed to an antigenic material occurring in the test population of cells). Any binding of the primary control antibody would hopefully be due to the general molecular characteristics of that subclass and therefore represent the nonspecific binding characteristics of the particular monoclonal antibodies employed.

It is also preferable that the absolute amount of primary control antibody should match the amount of antigen directed primary antibody used. It is desirable that the final concentration of all primary antibodies, control and antigen directed, match for all treatments. In this Example, the primary control antibody was a 1 mg/ml solution which matched the concentration of the preparations obtained from the supplier. Therefore, equivalent volumes of all primary antibody preparations could be used.

Protocol:

Sieving:

The 4 cc of callus tissue was suspended in a few mls of PBS and worked through a 200 micron nylon sieve with a gloved finger—the glove was freshly washed before use. Cells were rinsed through the sieve with PBS.

Treatments

The sieved callus cells were centrifuged in a 15 ml conical bottom plastic centrifuge tube (Corning #25310–15, Corning, N.Y., or an equivalent). The supernatant was discarded. The resulting pellet was suspended in 10 to 12 mls of freshly made blocking buffer for about 30 minutes and mildly agitated. After the blocking step, the cells were evenly distributed between five centrifuge tubes (Corning #25310–15, Corning, N.Y., or an equivalent). The volume in each tube was adjusted to 5 ml with blocking buffer.

Tube #1: Secondary Control

Treatment with secondary antibody only (Sheep anti-Mouse IgG coated Dynal beads)

Tube #2: Primary/Secondary Control

Treatment with primary control antibody (Mouse IgG2a kappa, 1 mg/ml, purified myeloma immunoglobulins) and secondary antibody (Sheep anti-Mouse IgG coated Dynal beads)

Tube #3: Anti-Taxol Treatment (Test sample 1)

Treatment with anti-taxol antibody and secondary antibody

Tube #4: Anti-Baccatin Treatment (Test sample 2)

Treatment with anti-baccatin antibody and secondary antibody

Tube #5: Anti-Taxane Treatment (Test sample 3)

Treatment with anti-taxane antibody and secondary antibody

Labeling Procedure:

Secondary control sample: nothing was added.

Primary/secondary control: 25 ul of mouse IgG2a kappa control antibody was added. Test samples: 25 ul of mouse anti-taxol (Hawaii Biotechnology, TA12) was added to test sample 1; 25 ul of mouse anti-baccatin (Hawaii Biotechnology, TA13) was added to test sample 2; 25 ul of mouse anti-taxane (Hawaii Biotechnology, TA14) was added to test sample 3. Samples were incubated for about 1 hour at room temperature with mild agitation, and then rinsed at least 3 times with PBS, pH 7.0. 4.5 ml of blocking buffer was added to each tube and the tubes were incubated for about 10 minutes at room temperature with gentle agitation. At this point, 0.5 ml of washed and evenly suspended Dynal beads was added to each of the five tubes. The tubes were incubated for about 1 hour at room temperature with sufficient agitation to keep the Dynal beads well suspended. At the end of the incubation period, about 5 to 7 ml of PBS was added to each of the tubes.

Isolation of Labeled Cells:

To capture the bead labeled cells, the magnet was taped to the middle, top side of the tube while the tube was held at a 45 degree angle. Since some unlabeled cells would be expected to be caught in the flow of beads and bead labeled cells towards the magnet, the tube was rocked gently (while the magnet was kept positioned above the tube) to dislodge any unlabeled cells and allow them to fall down and away from the magnet. When it appeared that most of the beads were attracted to the magnet, the tube was raised to its normal vertical position and as much of the free cells and liquid removed with a pipet as was possible without disturbing the captured fraction. The magnet was removed and 10 ml of PBS added to the tube. The tube was gently agitated for about 30 seconds while being careful to evenly suspend the cells and beads. This capture process for the bead labeled cells was then repeated and the loose cells and liquid once again removed. The beads and labeled cells remaining were resuspended in 2 to 3 mls of PBS and the contents of each tube transferred to a marked, individual well in a 6 well multiwell plate.

Using a glass Pasteur pipet and a stereo microscope, labeled cells were collected individually. This reduced the number of loose beads that were carried to the fixation and mounting steps. This is important because loose beads can settle on the surface of the cells and falsely label the cell surface. Preferably, this step is repeated at least twice to reduce the number of loose beads mixed with the labeled cells.

Mounting and Fixation:

The cells were suspended in about 100 ul of PBS and pipetted onto a polylysine coated Thermanox coverslip placed in a Petri dish. Care should be taken to avoid clumping the cells.

All of the excess fluid on the coverslip was gently drawn off with a 10–100 ul pipetman set to 100 ul, with the pipet held almost vertically against the coverslip. Care was taken not to draw in the cells and other particles. The cells and other specimens on the coverslip were drawn down onto the surface as the fluid was removed. 5 ul of 4% glutaraldehyde in PBS pH 7.0 was very carefully added to the cells by touching the tip of a micropipet to the edge of the coverslip and slowly adding the glutaraldehyde. Close attention was paid to the flow of the glutaraldehyde on the coverslip to ensure it spread evenly and contacted all the cells.

The Petri dish was covered and set aside for about 10 minutes. Another 5 ul of glutaraldehyde solution was added to each coverslip and allowed to react for another 10–15 minutes at room temperature. Each coverslip was gently flooded with about 200–300 ul of 4% glutaraldehyde in PBS pH 7.0, and allowed to react for about 15–30 minutes. The glutaraldehyde was then gently removed from each coverslip with a pipetman. The entire Petri dish was gently flooded with reagent grade water, the water was removed with a pipet, and the dish was again flooded. The cells remained well attached to the coverslip, and were allowed to sit overnight.

Serial dehydration was then performed using the following percentage solutions of EtOH: 20%, 40%, 60%, 80%, 95%, 100%. Dehydration was finished with critical point drier. The coverslips were then attached to color coded aluminum stubs with carbon coated "stickies". The specimen stubs were lightly coated with chromium using an ion beam sputter coater (VCR Group, Inc., San Francisco, Calif.), and examined at 10 kV using S-4500 field emission scanning electron microscope (Hitachi), equipped with an ultra-low voltage backscattered electron detector (GW Electronics, Norcross, Ga.). Images were captured using the PrinterFace frame-grabber board and software (GW Electronics), and edited with Adobe Photoshop.

EXAMPLE 2

This example describes a process for enhanced recovery of cell products, such as drugs.

First, a cell biomass is established using standard cell and tissue culture methods or other methods of biomass generation. Preferably, the source should be a genetic variety known as a high producer of the drug or other desired product (for ease of reference, the cells producing the drug or other product will be called "drug producing cells" and their product as a "drug" for the remainder of this example whether the product is a drug or another useful product.

Second, the drug-producing cells are labeled and isolated using antibody-coated Dynabeads® (Dynal) or other technology based on specifically contacting and labeling portions of the drug accessible on or in the cell wall, typically because the drug is embedded in the cell wall. The labeling may be by magnetic beads, as explained in the previous example, or may be by affinity chromatography or other conventional techniques known in the art.

Third, once isolated, the biomass responsible for drug production and cell-free drug-laden materials can be removed from the magnetic beads or other labeling means by standard enzymatic and/or competitive antibody reactions. Preferably, the biomass of the cells producing the drug is then increased, or "scaled up."

Fourth, the drug productive biomass is maintained at interphase using plant growth regulators. In this example, chlorsulfuron was used. Interphase processing reduces materials and energy required for new cell division and growth, and redirects cell functions towards drug production (that is, drug production is separated from growth requirements).

Fifth, preferably, cell viability and adaptive plasticity is maintained by the addition of media supplements that provide substrates for drug production or that prevent programmed cell death. In a preferred embodiment, the media supplement for this purpose is zinc, which competes with calcium activated proteases involved in apoptosis. Zinc can be added in any of several convenient forms, for example, as a mineral or organic salt. In preferred embodiments the salt is the sulfate or glucoronate salt. The zinc should be added as a trace element in the mg per liter range. Other anti-apoptosis agents, such as polyamines, are known in the art and can be used in this method. An agent can also be added to protect cell membranes from osmotic stress. In a preferred embodiment, the agent is betaine, which is preferably added to a concentration in the mg to gram per liter range. Other agents which can be used as osmotic pressure protectants are known in the art and include amino acids, such as proline, and sugars, such as trehalose, inositol, or mannitol.

EXAMPLE 3

This example shows the use of cell-free drug laden material isolated after step 3 of the preceding example. Using magnetic beads, affinity labeling, or other means known in the art, the cell free materials (cellular debris in the form of particles, membranes and other matrices) containing the drugs of interest and their precursors can be recovered. This material is bound to catalytic surfaces or used by the cell to dispose of toxic compounds. In some cases, the cell-free materials may contain enzymes for the final assembly of complex drugs or for their subsequent conversion to other natural products. In this example, magnetic beads were used, as described in example Other substrates, enzymes, etc., may be added to the materials to facilitate the chemical conversion of natural products to other novel compounds. Polymeric matrices associated with drug production are removed from cells and can be fractionated by their buoyant density or captured using paramagnetic beads, or affinity columns. The cell-free material can be optimized for reactivity (e.g. pH, oxygen, substrate levels, etc.). Process controls for this step will benefit from the addition of cyclodextrins. This material can be used for semisynthesis or chemical conversion of the bound drugs. Further, the matrix can be used to recover enzymes responsible for final drug assembly. Through amino acid sequencing of the isolated enzymes, the corresponding genes may be identified and used for varied genetic engineering purposes.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of identifying taxane-producing plant material in a sample, the method comprising the steps of contacting the plant material with an antibody which specifically binds taxanes present on plant cell walls.

2. The method of claim 1, further comprising the step of isolating the taxane-producing plant material from other material in the sample.

3. The method of claim 2, wherein the step of isolating is carried out using a paramagnetic bead to which a secondary antibody is bound.

4. The method of claim 3, wherein the secondary antibody is sheep anti-mouse IgG.

5. The method of claim 1, wherein the plant material comprises plant cells.

6. The method of claim 5, wherein the plant cells are Taxus cells.

7. The method of claim 5, wherein the cells are tissue culture cells.

8. The method of claim 5, further comprising the step of isolating high taxane-producing cells from low taxane-producing cells.

9. The method of claim 1, wherein the antibody is a monoclonal a monoclonal antibody selected from the group consisting of TA12, TA13, and TA14.

10. The method of claim 1, wherein the antibody is polyclonal.

11. A method of increasing taxane production in a plant cell culture, the method comprising growing the plant cell culture in a complete plant growth medium comprising an inhibitory compound.

12. The method of claim 11, wherein the inhibitory compound is an herbicide.

13. The method of claim 12, wherein the herbicide is chlorsulfuron.

14. The method of claim 13, wherein the chlorsulfuron is present at a concentration of between about $10^{-12}$M and about $10^{-6}$M.

15. The method of claim 11, further comprising adding a cell stress reductant to the complete plant growth medium.

16. The method of claim 11, wherein the plant cell culture comprises Taxus cells.

17. The method of claim 11, further comprising the step of isolating taxane producing plant cells from other cells in the culture using an antibody that specifically binds taxanes present in the cell wall of the plant cells.

18. The method of claim 17, wherein the step of isolating is carried out using a paramagnetic bead to which a secondary antibody is bound.

19. The method of claim 18, wherein the secondary antibody is sheep anti-mouse IgG.

* * * * *

UNITED STATES PATENT AND TRADEMARK OFFICE
CERTIFICATE OF CORRECTION

PATENT NO.    : 5,981,777
DATED         : November 9, 1999
INVENTOR(S)   : Don J. Durzan; Frank F. Ventimiglia It is certified that error appears in the above-identified patent and that said Letters Patent is hereby corrected as shown below:

In column 1, at line 10, insert :
--This invention was made with Government support under Grant No. NAG 9-825, awarded by NASA. The Government has certain rights in this invention.--

Signed and Sealed this

Fourteenth Day of November, 2000

Attest:

Q. TODD DICKINSON

Attesting Officer

Director of Patents and Trademarks